(12) United States Patent
Maeng

(10) Patent No.: US 12,174,915 B1
(45) Date of Patent: Dec. 24, 2024

(54) PROGRESSIVE MACHINE LEARNING USING A QUALIFIER

(71) Applicant: Wells Fargo Bank, N.A., San Francisco, CA (US)

(72) Inventor: Joon Maeng, Newcastle, WA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 1018 days.

(21) Appl. No.: 17/061,220

(22) Filed: Oct. 1, 2020

(51) Int. Cl.
| | |
|---|---|
| G06F 3/048 | (2013.01) |
| G06F 3/0482 | (2013.01) |
| G06F 18/21 | (2023.01) |
| G06F 18/214 | (2023.01) |
| G06N 20/20 | (2019.01) |
| G16H 50/20 | (2018.01) |

(52) U.S. Cl.
CPC ........ G06F 18/2178 (2023.01); G06F 3/0482 (2013.01); G06F 18/2148 (2023.01); G06N 20/20 (2019.01); G16H 50/20 (2018.01)

(58) Field of Classification Search
CPC ............ G06N 3/08; G06N 20/00; G06N 3/10; G06N 5/02; G06N 5/01; G06N 5/04; G06F 3/0482; G06F 3/04847
See application file for complete search history.

(56) References Cited

U.S. PATENT DOCUMENTS

| | | | | |
|---|---|---|---|---|
| 8,489,632 | B1 * | 7/2013 | Breckenridge | G06F 18/25 707/777 |
| 9,111,223 | B2 * | 8/2015 | Schmidt | G06N 20/00 |
| 9,336,494 | B1 * | 5/2016 | Purpura | G06N 20/00 |
| 10,121,104 | B1 * | 11/2018 | Hu | G06N 3/045 |
| 10,372,572 | B1 * | 8/2019 | Kesarwani | G06F 11/261 |
| 10,643,749 | B1 * | 5/2020 | Warner | G06N 5/041 |
| 10,685,260 | B1 * | 6/2020 | Adelaar | G06F 18/2148 |

(Continued)

FOREIGN PATENT DOCUMENTS

| | | |
|---|---|---|
| WO | 201869736 A1 | 4/2018 |
| WO | 202069051 A1 | 4/2020 |

OTHER PUBLICATIONS

Fayek et al., "Progressive learning: A deep learning framework for continual learning", Neural Networks, vol. 128, Available online May 18, 2020, 13 pp.

(Continued)

*Primary Examiner* — Steven B Theriault
(74) *Attorney, Agent, or Firm* — Shumaker & Sieffert, P.A.

(57) ABSTRACT

This disclosure describes techniques in which an artificially intelligent system includes a progressive machine learning model. In some examples, a system includes both a static and progressive model, each trained to make predictions or other assessments through machine learning techniques. The progressive model may be progressively updated, modified, and/or improved through additional training data or training examples, which may be derived from a local source and/or from one or more remote sources that may be chosen by a qualifier. The qualifier may be a human decision-maker that chooses, selects, and/or evaluates potential data or new training examples for use in updating the progressive model. The qualifier may, in other examples, be an artificially intelligent system trained to perform the functions of the qualifier.

18 Claims, 7 Drawing Sheets

(56) References Cited

U.S. PATENT DOCUMENTS

| | | | |
|---|---|---|---|
| 10,726,359 B1* | 7/2020 | Drouin | G16H 50/30 |
| 10,811,139 B1* | 10/2020 | Wang | G06N 20/20 |
| 10,817,791 B1* | 10/2020 | Shoemaker | G06F 21/316 |
| 11,144,940 B2* | 10/2021 | Flora | G06Q 30/0204 |
| 11,410,073 B1* | 8/2022 | Narsky | G06N 20/00 |
| 11,526,261 B1* | 12/2022 | Leach | G06F 17/18 |
| 11,621,085 B1* | 4/2023 | Gottula | H04L 67/34 |
| | | | 706/11 |
| 2013/0212542 A1* | 8/2013 | Baughman | G06F 3/04883 |
| | | | 715/866 |
| 2014/0249761 A1* | 9/2014 | Carroll | G16B 20/00 |
| | | | 702/19 |
| 2014/0365403 A1* | 12/2014 | Demuth | G06N 20/00 |
| | | | 706/11 |
| 2015/0379429 A1* | 12/2015 | Lee | G09B 5/00 |
| | | | 706/11 |
| 2016/0232457 A1* | 8/2016 | Gray | G06F 16/26 |
| 2016/0379119 A1* | 12/2016 | Kumar | G06F 11/008 |
| | | | 706/46 |
| 2017/0178019 A1* | 6/2017 | Duggan | G06F 8/60 |
| 2017/0193066 A1* | 7/2017 | Zhu | G06F 16/254 |
| 2017/0270418 A1* | 9/2017 | Reschke | G06F 3/04847 |
| 2017/0323216 A1* | 11/2017 | Fano | G06N 20/00 |
| 2017/0337464 A1 | 11/2017 | Rabinowitz et al. | |
| 2018/0314915 A1* | 11/2018 | Cai | G06N 5/022 |
| 2018/0365578 A1* | 12/2018 | Naughton | G06N 5/022 |
| 2019/0050728 A1 | 2/2019 | Sim et al. | |
| 2019/0057408 A1* | 2/2019 | Flora | G06N 20/00 |
| 2019/0129397 A1* | 5/2019 | Horiwaki | G05B 19/41885 |
| 2019/0228126 A1* | 7/2019 | Oh | G06F 30/327 |
| 2019/0244127 A1 | 8/2019 | Amado et al. | |
| 2019/0258904 A1* | 8/2019 | Ma | G06F 18/24133 |
| 2019/0294626 A1* | 9/2019 | Wickizer | G06F 16/9536 |
| 2020/0012962 A1* | 1/2020 | Dent | G06F 9/5011 |
| 2020/0050943 A1* | 2/2020 | Ishii | G06N 3/08 |
| 2020/0065712 A1 | 2/2020 | Wang et al. | |
| 2020/0110982 A1* | 4/2020 | Gou | G06N 3/088 |
| 2020/0175354 A1* | 6/2020 | Volodarskiy | G06N 3/08 |
| 2020/0210771 A1* | 7/2020 | Zeng | G06N 20/20 |
| 2020/0334262 A1* | 10/2020 | DiBenedetto | G06F 16/5838 |
| 2020/0337625 A1* | 10/2020 | Aimone | A61B 5/7267 |
| 2020/0387812 A1* | 12/2020 | Lewis | G06N 20/20 |
| 2020/0401886 A1* | 12/2020 | Deng | G06N 3/045 |
| 2021/0012196 A1* | 1/2021 | Lalitha | G06N 7/01 |
| 2021/0081819 A1* | 3/2021 | Polleri | G06N 5/022 |
| 2021/0081828 A1* | 3/2021 | Lopez De Prado | G06N 7/01 |
| 2021/0082577 A1* | 3/2021 | Sharifi | G06N 20/00 |
| 2021/0149363 A1* | 5/2021 | Chen | B23K 3/0638 |
| 2021/0158205 A1* | 5/2021 | Farchi | G06N 5/04 |
| 2021/0240892 A1* | 8/2021 | Meinders | G06F 30/27 |
| 2021/0249138 A1* | 8/2021 | Hayashitani | G16H 50/30 |
| 2021/0316185 A1* | 10/2021 | McKenna | G06F 3/0482 |
| 2021/0356920 A1* | 11/2021 | Takamatsu | G05B 13/048 |
| 2022/0101186 A1* | 3/2022 | Sharma Mittal | G06V 10/751 |
| 2022/0246302 A1* | 8/2022 | Fukui | A61B 5/7264 |
| 2022/0277192 A1* | 9/2022 | Gou | G06N 3/04 |
| 2022/0405606 A1* | 12/2022 | Suzuki | G06N 3/045 |
| 2023/0048301 A1* | 2/2023 | Kotolyan | G06F 3/0482 |
| 2023/0063311 A1* | 3/2023 | Horiguchi | G06N 5/022 |

OTHER PUBLICATIONS

Vartak et al., "MODELDB: A System for Machine Learning Model Management", HILDA'16, Jun. 26, 2016, 3 pp.

Zeng et al., "Progressive sampling-based Bayesian optimization for efficient and automatic machine learning model selection", Health Information Science and Systems, vol. 5, Sep. 2017, 21 pp.

* cited by examiner

PROGRESSIVE MACHINE LEARNING USING A QUALIFIER

TECHNICAL FIELD

This disclosure relates to machine learning, and more specifically, refining machine learning models with training data.

BACKGROUND

Machine learning is the field of study in Artificial Intelligence (AI) that gives computers the capability to learn without being explicitly programmed, relying on patterns and inference instead. Machine learning algorithms build a mathematical model based on sample data, known as "training data," in order to make predictions or decisions without being explicitly programmed to perform the task.

SUMMARY

This disclosure describes techniques in which an artificially intelligent system includes a progressive machine learning model. In some examples, such a system includes both static and progressive models, each trained to make predictions or other assessments through machine learning techniques. Predictions made by the static and progressive models may be presented to a user through a user interface, enabling the user to see, evaluate, and/or choose which of the predictions generated by each model to consider and/or use.

As described herein, the progressive model may be progressively updated, modified, and/or improved through additional training data or training examples, at least some of which may be derived from a local source and/or from one or more remote sources that may be chosen by a qualifier. A local source may correspond to a user of the system, such as a professional or other practitioner in the relevant field. Data from such a local source may therefore include data obtained, collected, and/or created by a user of the system in connection with activities performed as a professional or other practitioner. A remote source may be another system (e.g., operated by another professional) that is accessible over a network. In some examples, multiple networked systems may share field-developed training data directly by communicating with each other over a network. In other examples, a network-accessible data store may serve a clearinghouse for training data, receiving data over the network from systems seeking to publish data, and making data available to other systems over the network that seek to use the data.

The qualifier may be a human decision-maker that chooses, selects, and/or evaluates potential data or new training examples for use in updating the progressive model. The qualifier may, in other examples, be an artificially intelligent system trained to perform the functions of the qualifier, and may be trained based on data derived from historical selections made by a human qualifier. The training examples selected by the qualifier may be used to retrain and/or update the progressive model, thereby potentially improving the performance of the progressive model.

In some examples, this disclosure describes operations performed by a computing system in accordance with one or more aspects of this disclosure. In one specific example, this disclosure describes a method comprising applying, by a computing system, a first machine learning model to input data to make a first prediction; applying, by the computing system, a second machine learning model to the input data to make a second prediction, wherein the second machine learning model is derived from the first machine learning model; outputting, by the computing system, a user interface presenting information about the first prediction and the second prediction, and prompting a user to identify a preferred prediction; and responsive to receiving input identifying a preferred prediction, updating, by the computing system, the second machine learning model by using the input data and the preferred prediction as a new training example.

In another example, this disclosure describes a system comprising a storage system; and processing circuitry having access to the storage system and configured to: apply a first machine learning model to input data to make a first prediction; apply a second machine learning model to the input data to make a second prediction, wherein the second machine learning model is derived from the first machine learning model; output a user interface presenting information about the first prediction and the second prediction, and prompting a user to identify a preferred prediction; and responsive to receiving input identifying a preferred prediction, update the second machine learning model by using the input data and the preferred prediction as a new training example.

In another example, this disclosure describes a computer-readable storage medium comprising instructions that, when executed, configure processing circuitry of a computing system to apply a first machine learning model to input data to make a first prediction; apply a second machine learning model to the input data to make a second prediction, wherein the second machine learning model is derived from the first machine learning model; output a user interface presenting information about the first prediction and the second prediction, and prompting a user to identify a preferred prediction; and responsive to receiving input identifying a preferred prediction, update the second machine learning model by using the input data and the preferred prediction as a new training example.

The details of one or more examples of the disclosure are set forth in the accompanying drawings and the description below. Other features, objects, and advantages of the disclosure will be apparent from the description and drawings, and from the claims.

DETAILED DESCRIPTION

One of the more significant obstacles to implementing effective machine learning models is the volume and quality of the training data. Obtaining qualified data for training a machine learning model is often critical for a model's performance. Obtaining a sufficiently large amount of qualified data can be difficult in applications where the data is derived from work done by highly trained personnel. For instance, machine learning models that are used for diagnosing diseases from medical images often are trained using data from actual diagnoses performed by medical doctors. Qualified data associated with such diagnoses can be relatively rare or difficult to obtain. Yet without a large amount of qualified data, creating models that are capable of producing effective and accurate results is challenging.

Classical machine learning assumes that a model is trained with representative training data and data is no longer needed to improve the model after training. Such a process works well in many situations, particularly in situations involving well-known outcomes. For instance, if a model is trained to identify images that depict a common animal, such as a horse, classical machine learning algorithms can produce good results. However, if the model is to identify an object that changes over time, or evolves in some way (e.g., a mutating virus), models trained using classical machine learning techniques may be less effective, and may become less effective over time. Where the object or condition to be predicted changes or evolves significantly, a model trained using classical machine learning techniques might be ineffective.

Progressive machine learning uses more general assumptions about the data and training. Models trained using progressive techniques involve algorithms that update a trained model over time. In some cases, continual or frequent updating of the trained model is preferred. However, updating a model frequently is difficult, since frequent updates might require updating of models in the field by end-users. Yet end-users typically do not have sufficient knowledge about machine learning concepts or model development procedures, and generally cannot be relied upon to retrain models after such models are initially developed.

Yet in some cases, particularly in certain fields, end-users have access to—or may even create—new training examples. If such new training examples can be used to update models, the problem of obtaining qualified data may be alleviated or eliminated. This may be particularly true in fields where machine learning models require data derived from the work of highly-trained personnel working independently.

Figure 1:
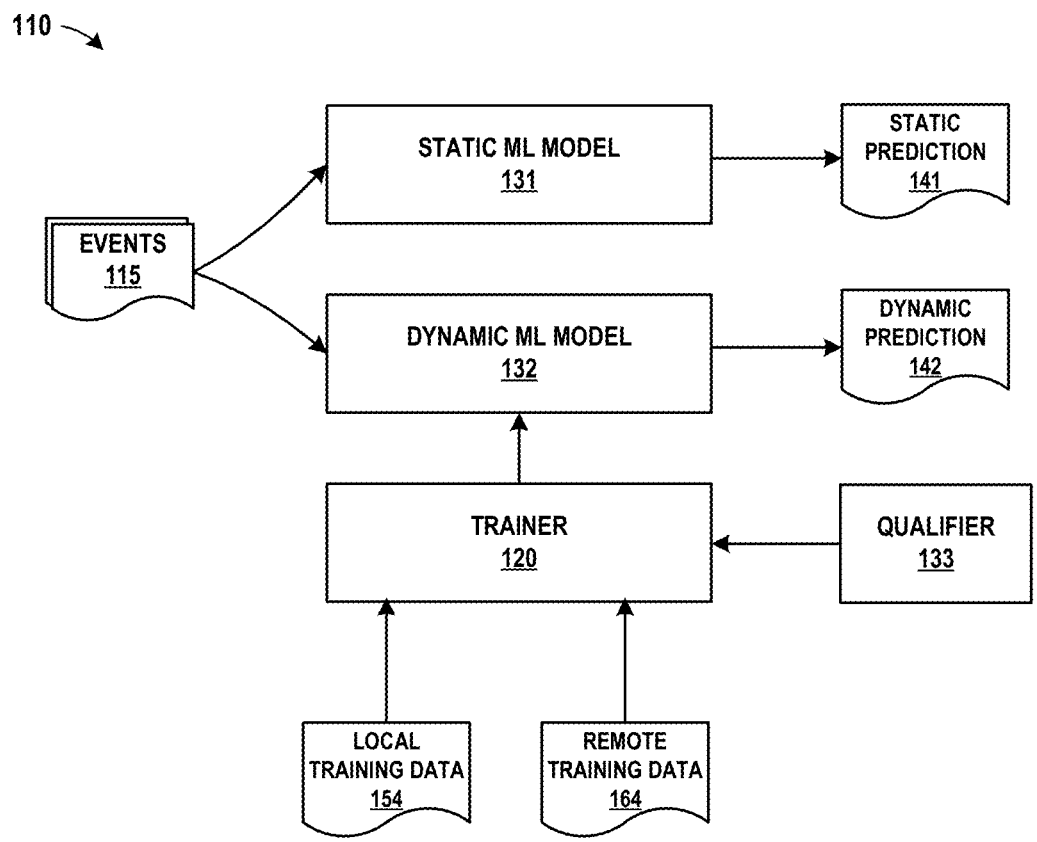
FIG. 1 is a block diagram illustrating an example system in which progressive machine learning techniques may be performed, in accordance with one or more aspects of the present disclosure.

FIG. 1 is a block diagram illustrating an example system in which progressive machine learning techniques may be performed, in accordance with one or more aspects of the present disclosure. The example of FIG. 1 illustrates static model 131 dynamic and/or progressive model 132, each of which may be derived from a model developed by a machine learning model developer (not shown). In some examples, the model developer may be a third party having sufficient expertise in a particular field to create a model to perform assessments or predictions in that field. The developer may distribute the developed model to end-users as a product or service.

Each of static model 131 and progressive model 132 may be presented with event data 115 in order generate a prediction. Static model 131 generates static model prediction 141 based on event data 115 and progressive model 132 generates progressive model prediction 142 also based on event data 115. Event data 115 may include data of the type that static model 131 and progressive model 132 are trained to use to generate predictions. Such data may, for a medical application, involve information about a patient, such as medical images, test results, data obtained by observing, examining, and/or taking biopsies from the patient, or other information. For a financial application, such data may involve information about general economic conditions as well as economic conditions and performance information for specific entities, corporations, securities, or investment vehicles.

In one example, the developer might have expertise in certain medical diagnoses techniques, and may develop static model 131 based on data collected by the developer. In such an example, the developer might release new versions of static model 131 to improve the diagnostic capability of static model 131 as new diagnosis data becomes available to the developer. Users of systems 110 might use the model to make diagnoses, but such users might have no control over the operation of static model 131.

When event data 115 is fed to static model 131, static model 131 produces one or more static model predictions 141 and makes such information available for use in guiding an end-user's own diagnosis. Accordingly, in some examples, static model 131 does not change once deployed. In other examples, however, static model 131 may be occasionally or periodically updated. Such updates, however, might be limited to incremental updates or new models distributed by the original developer of static model 131 (e.g., over network 205).

Progressive model 132, however, may be updated more aggressively once deployed. When initially deployed, progressive model 132 may be the same as or may be largely derived from static model 131. Progressive model 132 may, however, improve over time, as new data becomes available. For example, FIG. 1 illustrates trainer 120 used to update progressive model 132 based on local training data 154 and/or remote training data 164. Trainer 120 may accept input from qualifier 133, and based on the input, may select one or more instances of local training data 154 and/or remote training data 164 to train and/or retrain progressive model 132. Once retrained, progressive model 132 may be used to generate one or more progressive model predictions 142, but such progressive model predictions 142 may differ from those generated by progressive model 132 prior its retraining by trainer 120.

In some examples, qualifier 133 may be a human decision-maker. In other examples, qualifier 133 may itself be a model trained to perform selections of local training data 154 and/or remote training data 164. In such an example, qualifier 133 may be trained to mimic the selections and qualification decisions previously made by one or more human decision-makers.

Predictions made by progressive model 132 thus may change over time, and may improve if progressive model 132 is retrained using quality data. In some examples, progressive model 132 may therefore improve when deployed in the field (e.g., at a medical clinic or doctor's office, or at a financial investment firm). While progressive model 132 may initially be identical to static model 131, progressive model 132 may continually improve based on local training data 154 and/or remote training data 164, thereby resulting in a model that may be in at least some respects, superior to static model 131. Local training data 154 and remote training data 164 may, in some examples, be supplied or obtained in the field (e.g., at a medical clinic, doctor's office, or financial investment firm), and applied in the field to update progressive model 132.

In accordance with one or more aspects of the present disclosure, progressive model 132 may be retrained by trainer 120 using either local training data 154, remote training data 164, or both. For instance, in an example that can be described with reference to FIG. 1, static model 131 and progressive model 132 may be initially trained, by a third party developer, to perform medical diagnoses based on medical imaging data. Static model 131 may receive event data 115 and produce static model predictions 141 based on the training of static model 131 by the original developer of static model 131. Similarly, progressive model 132 may receive event data 115 and produce progressive model prediction 142 based on such training. Over time, however, a user (e.g., a doctor or other medical professional) may generate additional diagnoses based on the same event data 115, and use selected instances of such diagnoses as additional training examples (i.e., local training data 154). Trainer 120 may use such local training data 154 to retrain progressive model 132. In this example, the user of the system may act as qualifier 133.

Alternatively, or in addition, that same user (i.e., qualifier 133) may use one or more instances of remote training data 164 as field training data. In some examples, system 110 may be capable of communicating with other systems (not shown) over a network. Such other systems may be substantially similar to system 110, may also be operated by medical professionals, and may also be hosting machine learning models designed to perform diagnoses. For instance, continuing with the previously-described example, if system 110 performs medical diagnoses based on medical images in a hospital, one or more other systems (not shown) that perform similar diagnoses might be available within the same hospital. Remote training data 164 for system 110 may be derived from diagnoses performed by such other systems elsewhere within the hospital. In general, if a medical professional using system 110 trusts medical professionals within the same hospital to perform similar medical diagnoses, system 110 may receive instances of remote training data 164 from a network of systems within the hospital. Such instances of remote training data 164 may be used, by trainer 120, to retrain or update progressive model 132, and thereby improve the accuracy of progressive model 132.

Preferably, trainer 120 is capable of updating and/or retraining progressive model 132 without requiring machine learning expertise of any user in the field. In such an example, neither the medical professional nor qualifier 133 would need any significant expertise to enable trainer 120 to retrain progressive model 132 using local training data 154. In some examples, qualifier 133 and/or a medical professional might simply approve the use of instances of additional data (e.g., local training data 154 and/or remote training data 164) for retraining progressive model 132. Based on such approval, training module or trainer 120 may be a computing device and/or logic configured to update progressive model 132 appropriately using the additional data.

The techniques described herein may provide certain technical advantages. For instance, in fields where quality training data for use in training machine learning models is difficult to obtain, a group of networked systems 110 may provide additional access to qualified training data, potentially resolving a common need for machine learning data. As a result, system 110 may be used to refine progressive model 132 over time, resulting in a high quality and/or improved machine learning model. Further, in fields where the ground truth tends to evolve over time (e.g., as in the example of a mutating virus), system 110 or a group of networked systems 110 may enable effectively and timely updating of machine learning models, quickly and accurately picking up on evolving changes in ground truth, and thereby enabling model predictions that are based on the most up-to-date information.

Figure 2:
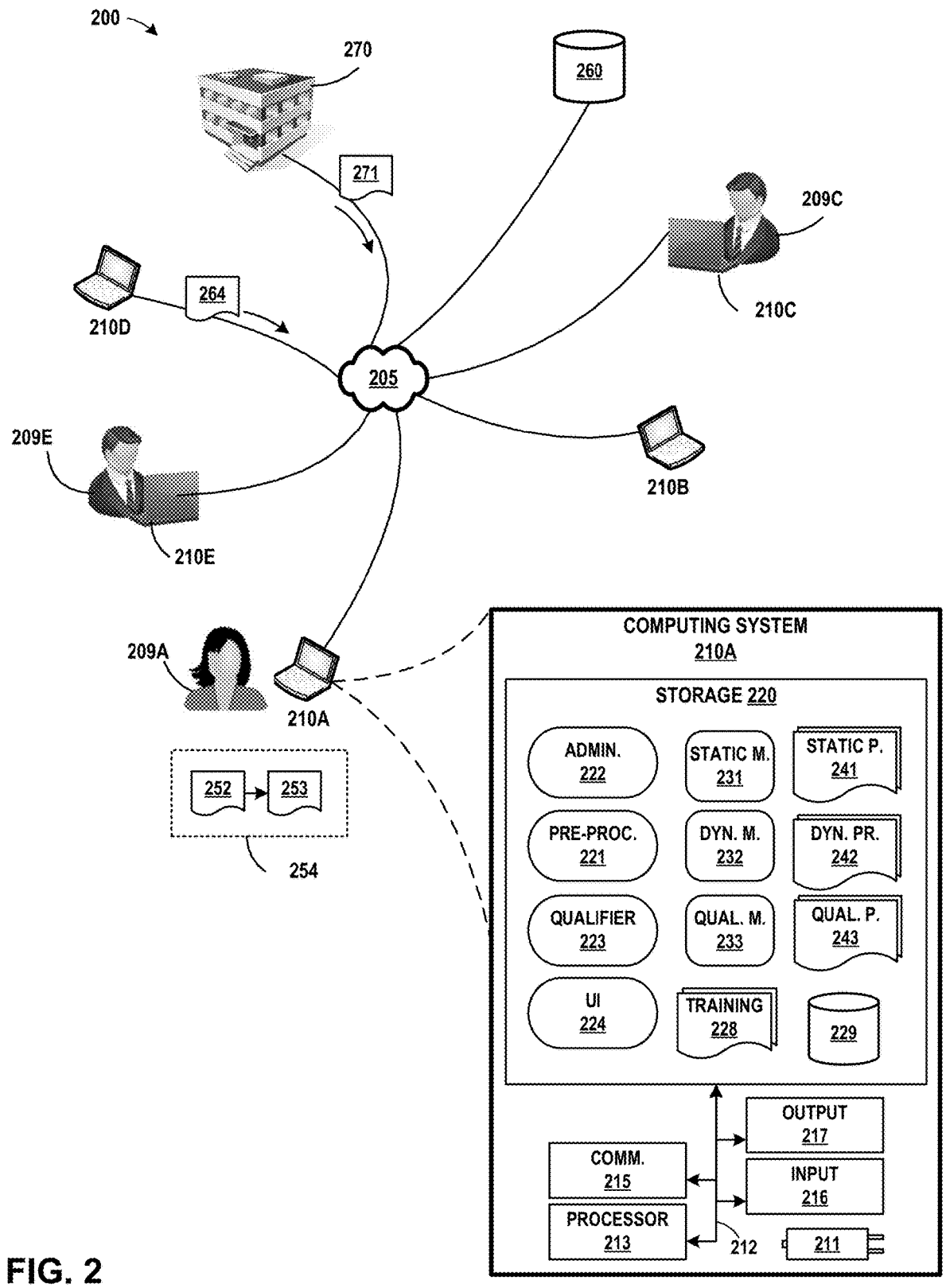
FIG. 2 is a block diagram illustrating an example networked system for use in implementing progressive machine learning techniques, in accordance with one or more aspects of the present disclosure.

FIG. 2 is a block diagram illustrating an example networked system for use in implementing progressive machine learning techniques, in accordance with one or more aspects of the present disclosure. In the example of FIG. 2, networked system 200 includes computing system 210A, computing system 210B, computing system 210C, computing system 210D, and computing system 210E ("computing systems 210"), all of which are capable of communicating over network 205. Each of computing systems 210 may be operated by a respective user (i.e., user 209A operates computing system 210A, user 209C operates computing system 210C, and user 209E operates computing system 210E). Clearinghouse 260 is also illustrated as being accessible over network 205, and may receive and publish information via network 205. Developer 270 may be a person, entity, or organization that develops models as described herein. In some examples, developer 270 may also be considered a computing system that performs operations as described herein. For ease of illustration, a limited number of computing systems 210, clearinghouses 260, and developers 270 are illustrated in FIG. 2, although techniques in accordance with one or more aspects of the present disclosure may be performed with many more of such systems.

Network 205 may be the internet, or may include or represent any public or private communications network or other network. For instance, network 205 may be a cellular, Wi-Fi®, ZigBee, Bluetooth, Near-Field Communication (NFC), satellite, enterprise, service provider, and/or other type of network enabling transfer of transmitting data between computing systems, servers, and computing devices. One or more of client devices, server devices, or other devices may transmit and receive data, commands, control signals, and/or other information across network 205 using any suitable communication techniques. Network 205 may include one or more network hubs, network switches, network routers, satellite dishes, or any other network equipment. Such devices or components may be operatively inter-coupled, thereby providing for the exchange of information between computers, devices, or other components (e.g., between one or more client devices or systems and one or more server devices or systems). Each of the devices or systems illustrated in FIG. 2 may be operatively coupled to network 205 using one or more network links. The links coupling such devices or systems to network 205 may be Ethernet, Asynchronous Transfer Mode (ATM) or other types of network connections, and such connections may be wireless and/or wired connections. One or more of the devices or systems illustrated in FIG. 2 or otherwise on network 205 may be in a remote location relative to one or more other illustrated devices or systems.

Each of computing systems 210 may be implemented as any suitable computing system, such as one or more server computers, workstations, desktop systems, mainframes, appliances, cloud computing systems, and/or other computing systems that may be capable of performing operations and/or functions described in accordance with one or more aspects of the present disclosure. In some examples, one or more of computing systems 210 represent a cloud computing system, server farm, and/or server cluster (or portion thereof) that provides services to client devices and other devices or systems. In other examples, one or more of computing systems 210 may represent or be implemented through one or more virtualized compute instances (e.g., virtual machines, containers) of a data center, cloud computing system, server farm, and/or server cluster.

Certain aspects of computing systems 210 are described below with respect to computing system 210A. Other computing systems 210 (e.g., one or more of computing systems 210B, 210C, 210D, and 210E) may be described similarly, and may also include the same, similar, or corresponding components, devices, modules, functionality, and/or other features. Descriptions of computing system 210A herein may therefore correspondingly apply to one or more other computing systems 210.

In the example of FIG. 2, computing system 210A includes power source 211, one or more processors 213, one or more communication units 215, one or more input devices 216, one or more output devices 217, and one or more storage devices 220. Storage devices 220 may include preprocessing module 221, model administration module 222, qualifier module 223, user interface module 224, static model 231, progressive model 232, qualifier model 233, one or more instances of training data 228, static model predictions 241, progressive model predictions 242, qualifier model predictions 243, and one or more data stores 229. One or more of the devices, modules, storage areas, or other components of computing system 210A may be interconnected to enable inter-component communications (physically, communicatively, and/or operatively). In some examples, such connectivity may be provided by through communication channels (e.g., communication channels 212), a system bus, a network connection, an inter-process communication data structure, or any other method for communicating data.

Power source 211 may provide power to one or more components of computing system 210A. Power source 211 may receive power from the primary alternating current (AC) power supply in a building, home, or other location. In other examples, power source 211 may be a battery or a device that supplies direct current (DC). In still further examples, computing system 210A and/or power source 211 may receive power from another source. One or more of the devices or components illustrated within computing system 210A may be connected to power source 211, and/or may receive power from power source 211. Power source 211 may have intelligent power management or consumption capabilities, and such features may be controlled, accessed, or adjusted by one or more modules of computing system 210A and/or by one or more processors 213 to intelligently consume, allocate, supply, or otherwise manage power.

One or more processors 213 of computing system 210A may implement functionality and/or execute instructions associated with computing system 210A or associated with one or more modules illustrated herein and/or described below. One or more processors 213 may be, may be part of, and/or may include processing circuitry that performs operations in accordance with one or more aspects of the present disclosure. Examples of processors 213 include microprocessors, application processors, display controllers, auxiliary processors, one or more sensor hubs, and any other hardware configured to function as a processor, a processing unit, or a processing device. Computing system 210A may use one or more processors 213 to perform operations in accordance with one or more aspects of the present disclosure using software, hardware, firmware, or a mixture of hardware, software, and firmware residing in and/or executing at computing system 210A.

One or more communication units 215 of computing system 210A may communicate with devices external to computing system 210A by transmitting and/or receiving data, and may operate, in some respects, as both an input device and an output device. In some examples, communication unit 215 may communicate with other devices over a network. In other examples, communication units 215 may send and/or receive radio signals on a radio network such as a cellular radio network. Other methods of communication are also possible and are considered within the scope of this disclosure.

One or more input devices 216 may represent any input devices of computing system 210A not otherwise separately described herein. One or more input devices 216 may generate, receive, and/or process input from any type of device capable of detecting input from a human or machine. For example, one or more input devices 216 may generate, receive, and/or process input in the form of electrical, physical, audio, image, and/or visual input (e.g., peripheral device, keyboard, microphone, camera). One or more input devices 216 may generate or receive input from a keyboard, pointing device, voice responsive system, video camera, button, sensor, mobile input device, control pad, microphone, presence-sensitive screen, network, or any other type of device for detecting input from a human or machine. In some examples, input devices 216 may include one or more sensor components, such as medical sensors. Such input devices may also include one or more location sensors (GPS components, Wi-Fi® components, cellular components), one or more temperature sensors, one or more movement sensors (e.g., accelerometers, gyros), one or more pressure sensors (e.g., barometer), one or more ambient light sensors, and one or more other sensors (e.g., infrared proximity sensor, hygrometer sensor, and the like). Other sensors, to name a few other non-limiting examples, may include a heart rate sensor, magnetometer, glucose sensor, olfactory sensor, compass sensor, step counter sensor.

One or more output devices 217 may represent any output devices of computing system 210A not otherwise separately described herein. One or more output devices 217 may generate, receive, and/or process input from any type of device capable of detecting input from a human or machine. For example, one or more output devices 217 may generate, receive, and/or process output in the form of electrical and/or physical output (e.g., peripheral device, actuator). For computing devices that may be used by a user, one or more output devices 217 may generate, present, and/or process output in the form of tactile, audio, visual, video, and other output. Output devices 217 may include a sound card, video graphics adapter card, speaker, presence-sensitive screen, one or more USB interfaces, video and/or audio output interfaces, a display, or any other type of device capable of generating tactile, audio, visual, video, or other output (e.g., a haptic response, a sound, a flash of light, and/or images). Some devices may serve as both input and output devices. For example, a communication device may both send and receive data to and from other systems or devices over a network. Also, a touch-sensitive or presence-sensitive display may both detect input in the form of physical taps or gestures, and present output in the form of visual information.

One or more storage devices 220 within computing system 210A may store information for processing during operation of computing system 210A. Storage devices 220 may store program instructions and/or data associated with one or more of the modules described in accordance with one or more aspects of this disclosure. One or more processors 213 and one or more storage devices 220 may provide an operating environment or platform for such modules, which may be implemented as software, but may in some examples include any combination of hardware, firmware, and software. One or more processors 213 may execute instructions and one or more storage devices 220 may store instructions and/or data of one or more modules. The combination of processors 213 and storage devices 220 may retrieve, store, and/or execute the instructions and/or data of one or more applications, modules, or software. Processors 213 and/or storage devices 220 may also be operably coupled to one or more other software and/or hardware components, including, but not limited to, one or more of the components of computing system 210A and/or one or more devices or systems illustrated as being connected to computing system 210A.

In some examples, one or more storage devices 220 are temporary memories, which may mean that a primary purpose of the one or more storage devices is not long-term storage. Storage devices 220 of computing system 210A may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art. Storage devices 220, in some examples, also include one or more computer-readable storage media. Storage devices 220 may be configured to store larger amounts of information than volatile memory. Storage devices 220 may further be configured for long-term storage of information as non-volatile memory space and retain information after activate/off cycles. Examples of non-volatile memories include magnetic hard disks, optical discs, Flash memories, or forms of electrically programmable memories (EPROM) or electrically erasable and programmable (EEPROM) memories.

Model administration module 222 may perform functions relating to maintaining, training, and administering one or more models, including static model 231, progressive model 232, and/or qualifier model 233. Model administration module 222 may output information to preprocessing module 221 to prepare such information for use in generating one or more predictions (e.g., static model prediction 241, progressive model prediction 242, qualifier model prediction 243), or for use in training or retraining one or more models (e.g., progressive model 232 and/or qualifier model 233). Model administration module 222 may update or modify each of models based on other information, such as information received from developer 270. Model administration module 222 may also interpret input received by one or more of input devices 216, and perform corresponding actions to implement user commands (e.g., generating one or more of static model predictions 241, progressive model predictions 242, or qualifier model predictions 243, or retraining progressive models 232).

Preprocessing module 221 may perform functions relating to processing data for use as input to one or more models (e.g., static model 231, progressive model 232, or qualifier model 233) or for use as training data for training one or more of such models. In some examples, data collected in the field may be filtered or processed to address missing data, extremely large values, unorganized text data or noisy data. Preprocessing module 221 may also split potential training data into two non-overlapping sets, training data (used to train a machine learning model) and testing data (used to verify accuracy of predictions made by models).

Qualifier module 223 may perform functions relating to processing selections made by a user relating to training examples to be used in retraining progressive model 232. Qualifier module 223 may access one or more instances of training data 228 stored within storage device 220 that correspond to the selections. Qualifier module 223 may cause model administration module 222 to retrain progressive model 232 using the selected training examples. Qualifier module 223 may also train or retrain qualifier model 233 to select training examples from one or more instances of remote training data 264. In some examples, qualifier module 223 may train qualifier model 233 to mimic selections historically made by a human qualifier in the manner described herein.

User interface module 224 may manage user interactions with output device 217 and other components of computing system 210A. User interface module 224 may cause output device 217 to output various user interfaces for display or presentation or otherwise, as a user of computing system 210A views, hears, or otherwise senses output and/or provides input at output device 217. Output device 217 may detect input, and may output to user interface module 224 one or more indications of input as a user of computing system 210A interacts with a user interface presented at output device 217. User interface module 224 and output device 217 may interpret inputs detected at output device 217 and may relay information about the inputs detected at output device 217 to one or more associated platforms, operating systems, applications, and/or services executing at computing system 210A to cause computing system 210A to perform one or more functions.

Training data 228 may include information derived from data collected or created by a user of computing system 210A, which may, for example, be a medical, investment, or other expert. Training data 228 may also include information received in communications with one or more other computing systems 210, such as remote training data 264. In some examples, instances of training data 228 may be stored in data store 229, and made available, upon request, to one or more other modules of computing system 210A.

Data store 229 may represent any suitable data structure or storage medium for storing information related to training examples relevant to static model 231, progressive model 232, and/or qualifier model 233. The information stored in data store 229 may be searchable and/or categorized such that one or more modules within computing system 210A may provide an input requesting information from data store 229, and in response to the input, receive information stored within data store 229. Data store 229 may be primarily maintained by model administration module 222. Data store 229 may provide other modules with access to the data stored within data store 229, and/or may analyze the data stored within data store 229 and output such information on behalf of other modules of computing system 210.

Each of static model 231, progressive model 232, and qualifier model 233 may represent a trained model for making an assessment, diagnosis, selection, or other prediction on the basis of input data. Specifically, static model 231 generates one or more instances of static model predictions 241 based on data provided as input to static model 231. Progressive model 232 generates one or more instances of progressive model predictions 242 based on data provided as input to progressive model 232. Qualifier model 233 generates one or more instances of progressive model predictions 242 based on data provided as input to qualifier model 233.

In FIG. 2, static model 231 may correspond to a machine learning model trained or created by developer 270, which may be occasionally or periodically updated by developer 270. In some examples, static model 231 is based on or included within model information 271, which may be received over network 205 from developer 270. Progressive model 232 may correspond to a machine learning model that may also be at least initially created by developer 270 or another developer. As described herein, progressive model 232 may be occasionally, periodically, or continually updated based on additional training examples, as such examples become available. Qualifier model 233 may correspond to a machine learning model trained to perform the role of a qualifier, as described herein.

A machine learning model developer (e.g., developer 270) may collect training data and use the training data to develop a model that is useful for making predictions about future events or unknown conditions. For example, a developer may use machine learning techniques to predict movements of financial markets, make investment selections, make medical assessments or diagnoses, identify objects in images, classify images or other data, perform facial or voice recognition functions, predict the value of a house or other asset, or perform other tasks.

Typically, the performance of a model developed through machine learning depends on the quantity (and quality) of the data that is used to train the model. Appropriate training data for some tasks that can be performed by such model is plentiful, such as, for example images of animals (e.g., dogs, horses, or cows). Accordingly, machine learning algorithms trained to identify an animal in an image tend to perform well.

However, other training data is more difficult to acquire, particularly in situations where significant human expertise is needed in order to create the data, such as in situations where a trained human is needed to make an accurate assessment, diagnosis, or prediction on the basis of input data. In such situations, machine learning models tend to improve as more training data is available. Examples of situations in which training data tends to be difficult to acquire include the financial and medical fields. In finance, for example, an investment professional may have expertise, accumulated over a significant period of time, that benefits investment decisions. Similarly, in medicine, medical professionals may have expertise that enable them to make accurate medical diagnoses. Since there are a limited number of qualified investment and medical professionals making such assessments, training data is not as plentiful as in other situations. The Financial and medical scenarios described herein are merely examples, however, and there are many other situations that are within the scope of this disclosure where a lack of expertise and/or a lack of application of that expertise translates into a limited supply of quality training data.

In some examples, developer 270 may seek to develop a model to predict outcomes in a situation where training data is not readily available. For instance, in an example relevant to the medical field, developer 270 may develop a model that identifies abnormalities of various bodily organs, identifies and/or classifies cancerous growths, performs diagnoses, and/or identifies the cause of pain a patient may be suffering. In some examples, developer 270 might use machine learning algorithms to create a such model, where the model is trained to perform medical diagnoses based on information about the patient. Often the information about the patient includes or is derived from various types of medical imaging captured from the patient.

In one specific example that can be described for purposes of illustration, developer 270 may develop a model to determine whether a patient suffers from an affliction affecting joint mobility, such as osteoarthritis. Developer 270 may use medical imaging (e.g., x-ray images, magnetic resonance images, or other types of images) of a patient's knee as the basis for making such a diagnosis for that patient's knee. To generate such a model, developer 270 collects historical training examples, which may include many medical images of human knees (both healthy and arthritic knees). For each such image, the training data includes information about what is understood to be the correct diagnosis associated with that image (e.g., whether the knee is healthy or whether the knee is afflicted with some degree of osteoarthritis). Typically, the diagnosis associated with each instance or example of historical training data is or was determined by a medical professional trained to properly determine the stage of osteoarthritis associated with the knee.

Developer 270 may use machine learning techniques to develop such a model, using the diagnosis associated with each training example as ground truth for training a model. In some examples, developer 270 may use a supervised learning algorithm to analyze the training data (e.g., images of knees, each coupled with a diagnosis) and produce an inferred function. The inferred function or model can then be used for predicting a correct diagnosis from new images of a knee presented by future patients. In such an example, the model accepts one or more images of a knee as input, and then generates a predicted diagnosis (i.e., output) that indicates whether the knee is healthy or whether the knee is afflicted with some degree of osteoarthritis.

Once created, developer 270 may offer the model as a product or service, and distribute it to users, which may include doctors, hospitals, and medical clinics in the relevant medical field. For instance, in an example that can be described in the context of FIG. 2, developer 270 acquires historical training data and develops a model (e.g., a machine learning model) that can be used to determine whether a patient suffers from osteoarthritis based on an image of the patient's knee. Developer 270 outputs information about the developed model (i.e., model information 271) over network 205. Communication unit 215 of computing system 210A detects input and outputs an indication of input to model administration module 222. Model administration module 222 determines that the input corresponds to model information 271, and further determines that model information 271 is or includes information about a machine learning model that can be used to make predictions (i.e., osteoarthritis diagnoses) based on input images.

Once model information 271 is distributed to computing system 210A from developer 270, computing system 210A may be configured to use both a static and a dynamic machine learning model to make predictions. For instance, continuing with the example being described in the context of FIG. 2, model administration module 222 uses model information 271 to instantiate static model 231 at computing system 210A. Model administration module 222 uses model information 271 to also instantiate progressive model 232 at computing system 210A. In some examples, progressive model 232 may be the same as static model 231 (at least initially) and may even be a duplicate copy of static model 231.

Even with static model 231 and progressive model 232 instantiated at computing system 210A, user 209A may make a diagnosis of a patient's knee based on data collected by user 209A. For instance, still referring to the example being described in connection with FIG. 2, user 209A collects medical information from a new patient (i.e., "Patient A"), such as medical images of Patient A's knee (e.g., "local data 252"). In the example being described, user 209A (and each of users 209) may be a medical professional having expertise in making osteoarthritis diagnoses. User 209A assesses the information, and based on her experience and training, makes a diagnosis, possibly recording the diagnosis in medical chart or an electronic data store (e.g., as "local prediction 253"). In the example being described, user 209A determines that Patient A has severe osteoarthritis of the knee.

Computing system 210A may also be used to make a diagnosis of the patient's knee. For instance, referring again to the example being described with reference to FIG. 2, before or after making her own diagnosis (i.e., local prediction 253), user 209A presents local data 252 to computing system 210A as input. Input device 216 of computing system 210A detects input and outputs information about the input to model administration module 222. Model administration module 222 determines that the input corresponds to local data 252 and is intended to be used for making a diagnosis of Patient A. Model administration module 222 outputs local data 252 to static model 231, and causes static model 231 to be applied to local data 252. In some examples, model administration module 222 causes module 221 to preprocess local data 252. Static model 231 generates static model prediction 241 based on local data 252. Model administration module 222 also outputs local data 252 to progressive model 232, and causes progressive model 232 to be applied to local data 252. Progressive model 232 generates progressive model prediction 242 based on local data 252.

In an alternative embodiment, the network system 200 may work as a peer-to-peer network where there is no clearing house in the networked system 200. The networked computing systems 210 A 210B 210C 210D 210E may communicate with each other and share information selectively based on a configuration in the computing system. For instance, a first computing system 210C may establish a peer-to-peer network with a second communication system 210B and obtain information to use as remote source 154 for its trainer 120 from the second computing system 210B. In this embodiment, an administrator or administration module 222 may allow a user to configure a peer-to-peer network with other computing systems and choose information to use selectively.

FIG. 3A, FIG. 3B, FIG. 3C, and FIG. 3D are conceptual diagrams illustrating example user interfaces presented by a user interface device in accordance with one or more aspects of the present disclosure. Each of user interfaces 301A, 301B, 301C, and 301D ("user interfaces 301") may correspond to a user interface presented by an output device, such as display device 300, included as part of one or more of computing systems 210 of FIG. 2. Display device 300 may therefore be considered an example of output devices 217 illustrated in FIG. 2. In some examples, such as where display device 300 is a presence-sensitive display (e.g., a "touch screen"), display device 300 may also serve as an example of input device 216 illustrated in FIG. 2.

Figure 3A:
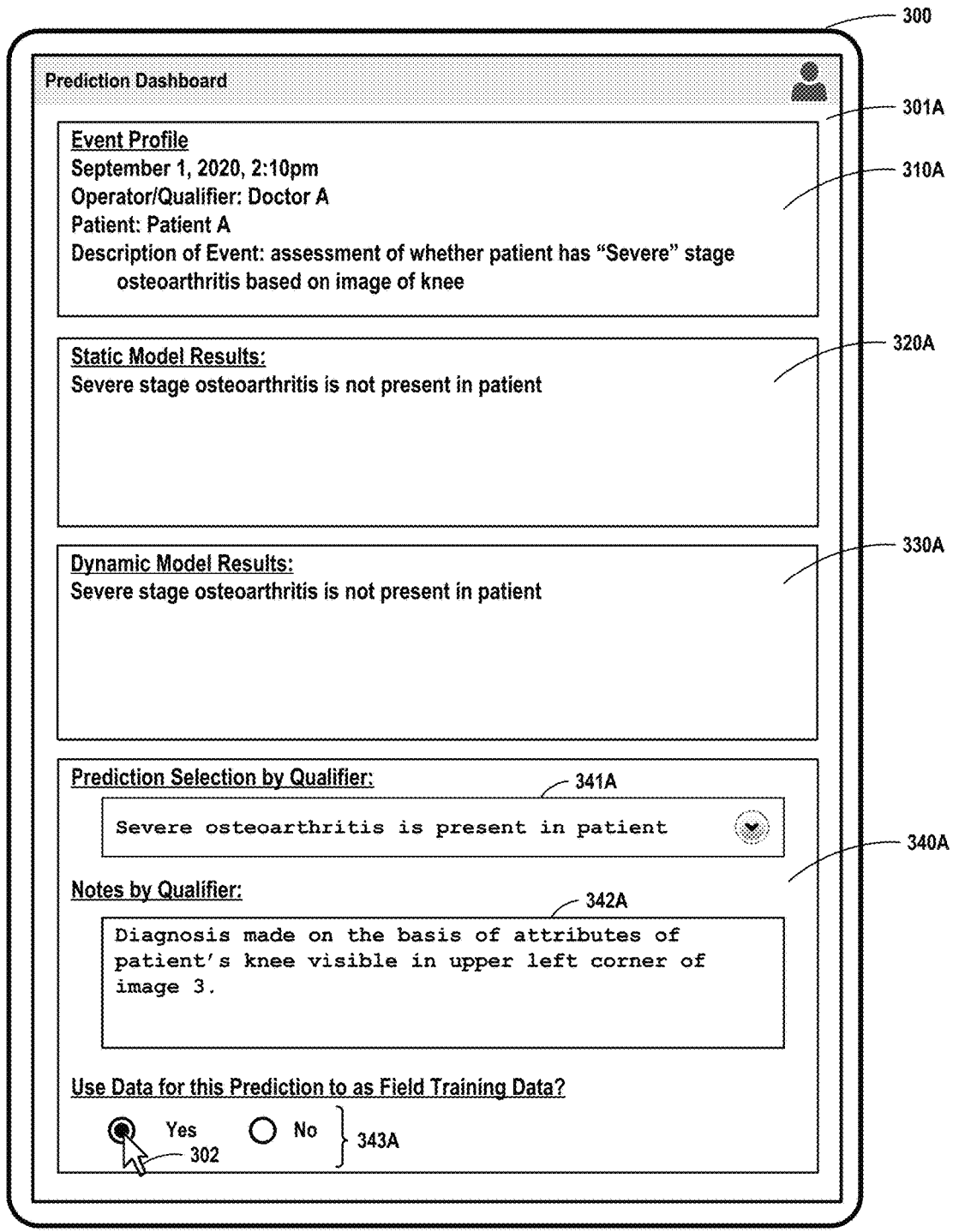
FIG. 3A, FIG. 3B, FIG. 3C, and FIG. 3D are conceptual diagrams illustrating example user interfaces presented by a user interface device in accordance with one or more aspects of the present disclosure.
Figure 3B:
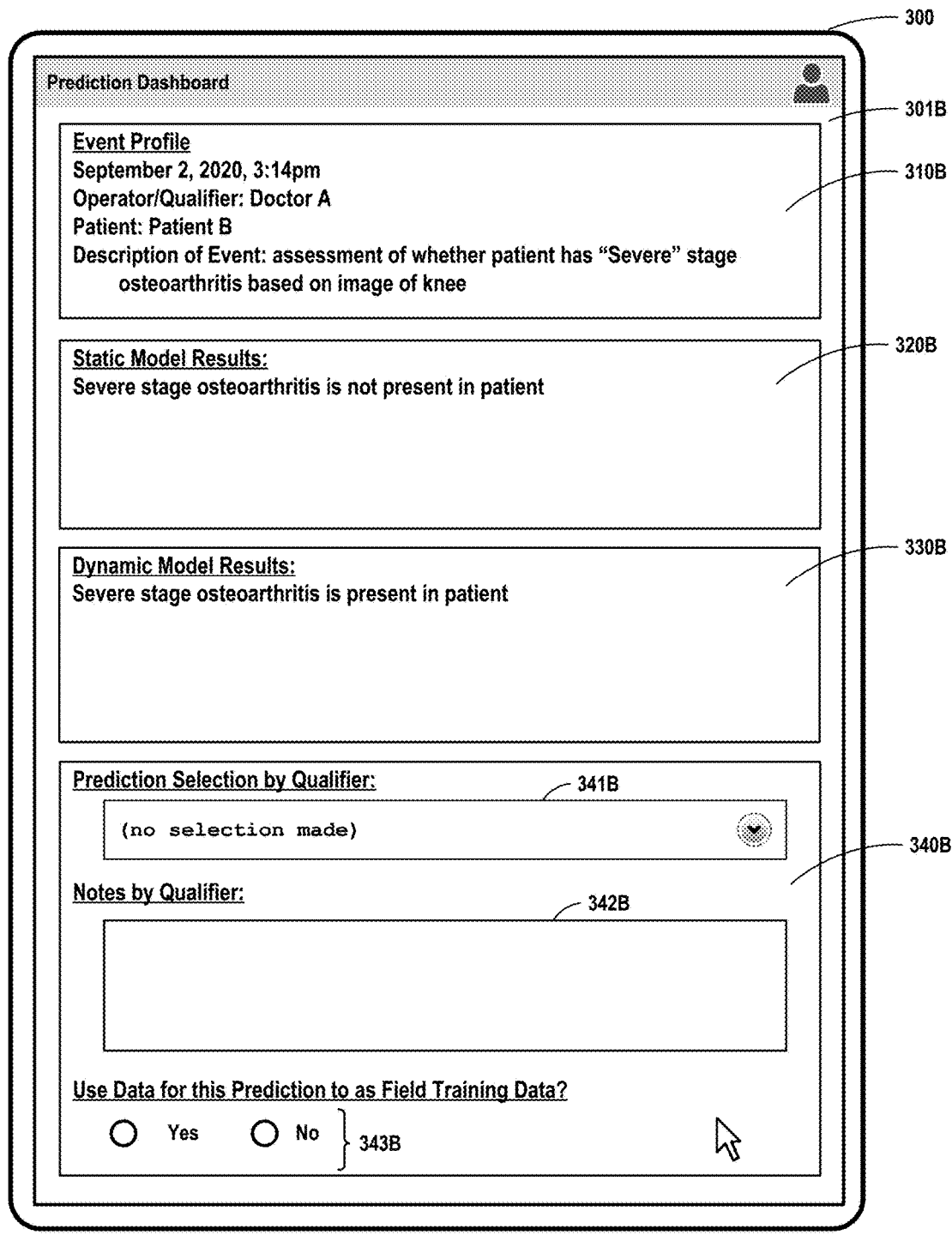
Figure 3C:
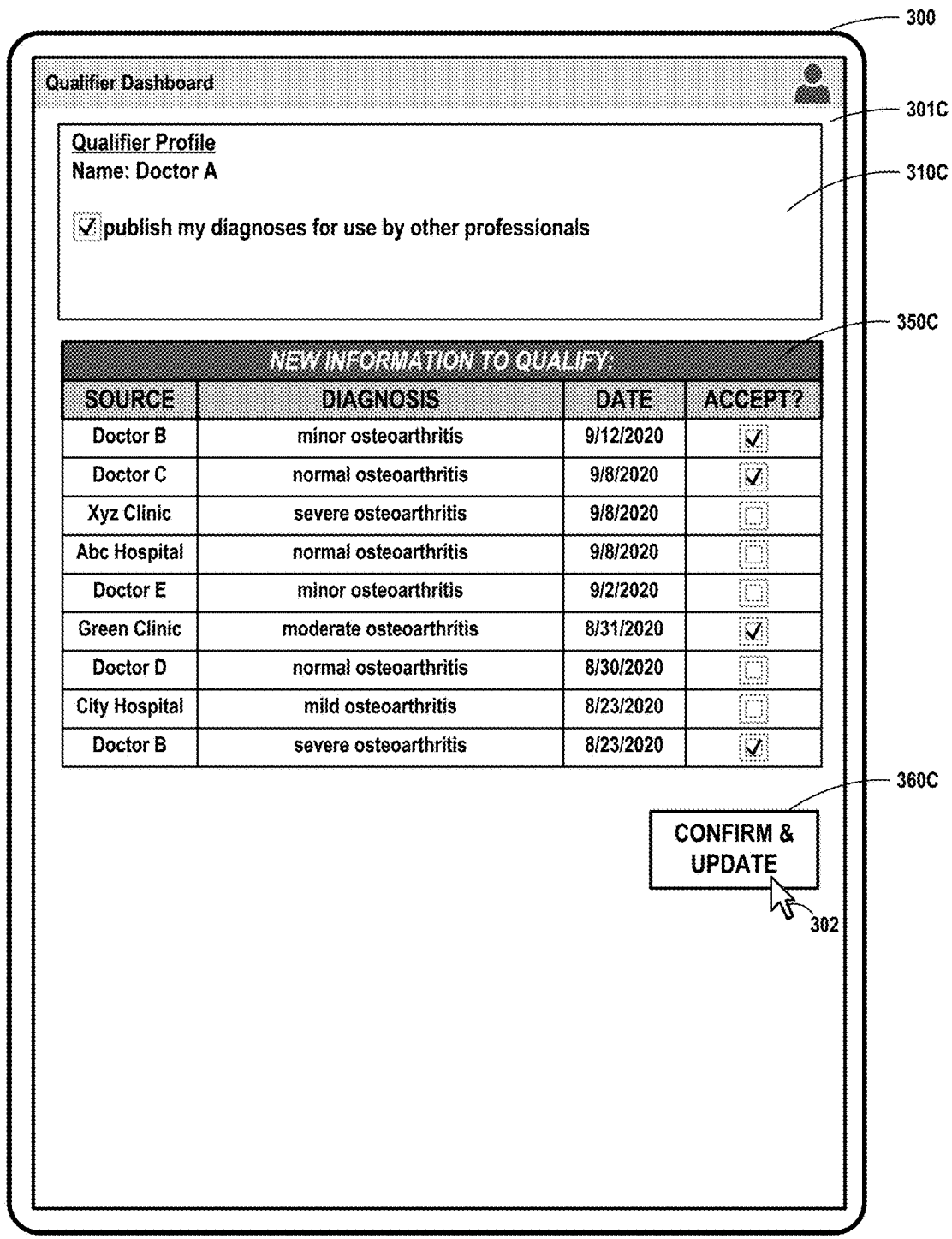
Figure 3D:
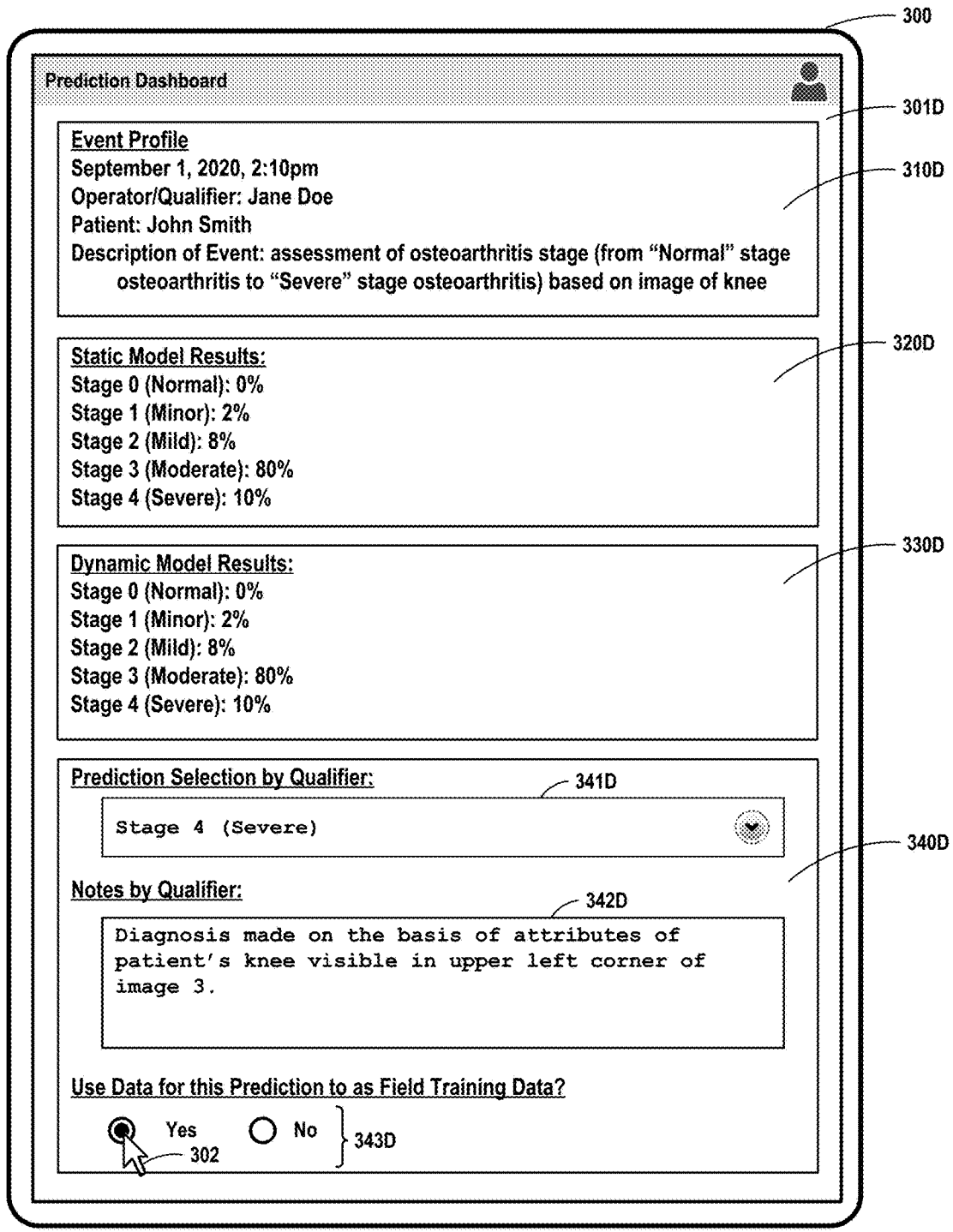

FIG. 3A is an example user interface illustrating predictions made by an example static model and an example progressive model, where the two predictions are the same. FIG. 3A also illustrates user interface features enabling selection of a preferred prediction by a user. FIG. 3B is another example user interface illustrating predictions by an example static model and an example progressive model, where the two predictions differ. FIG. 3C is an example user interface enabling a user to select or qualify new training data. FIG. 3D is an example user interface illustrating a different type of prediction: FIG. 3D illustrates predictions specifying a particular stage of osteoarthritis associated with a patient's knee.

Although the user interfaces illustrated in FIG. 3A, FIG. 3B, FIG. 3C, and FIG. 3D are shown as graphical user interfaces, other types of interfaces may be presented in other examples, including a text-based user interface, a console or command-based user interface, a voice prompt user interface, or any other appropriate user interface. One or more aspects of the user interfaces illustrated in FIG. 3A, FIG. 3B, FIG. 3C, and FIG. 3D may be described herein within the context of computing system 210A of FIG. 2.

In accordance with one or more aspects of the present disclosure, computing system 210A may present information about the diagnoses performed by computing system 210A. For instance, referring again to the example previously being described with respect to FIG. 2 and now also referring to FIG. 3A, model administration module 222 observes that static model 231 and progressive model 232 have generated static model prediction 241 and progressive model prediction 242, respectively, based on local data 252. Responsive to model administration module 222 observing that static model 231 and progressive model 232 have generated static model prediction 241 and progressive model prediction 242, respectively, model administration module 222 outputs to user interface module 224 information about the predictions. User interface module 224 uses the information to generate data sufficient to render a user interface on a display device. User interface module 224 uses the data to cause display device 300 to present user interface 301A at display device 300 as illustrated in FIG. 3A.

In FIG. 3A, user interface 301A presents information about the previously-described predictions or diagnoses performed by static model 231 and progressive model 232. To present such information, user interface 301A includes profile region 310A, static model region 320A, dynamic model region 330A, and qualifier region 340A. Profile region 310A identifies the patient being evaluated, describes a time and an operator (e.g., Doctor A or user 209A) and/or qualifier. Profile region 310A also provides information about what type of diagnosis is being performed. In the example being described, and as reported by profile region 310A, Patient A's knee is being evaluated to assess whether his knee has a "Severe" stage of osteoarthritis. Static model region 320A presents information about the prediction generated by static model 231 (i.e., static model prediction 241), and dynamic model region 330A presents information about the prediction generated by progressive model 232 (i.e., progressive model prediction 242).

User interface 301A for FIG. 3A also allows a user (e.g., user 209A or a user acting on behalf of user 209A) to input information about the diagnosis that was performed by user 209A. For example, as shown in FIG. 3A, qualifier region 340A of user interface 301A includes prediction drop-down box 341A, notes text box 342A, and prediction selection controls 343A. Prediction drop-down box 341A enables user 209A to input her diagnosis (i.e., corresponding to local prediction 253). The selection made in prediction drop-down box 341A may represent user 209A's preferred prediction. In some examples, such a preferred prediction may correspond to or be the same as the prediction presented in either static model region 320A or dynamic model region 330A. In other examples, such a preferred prediction may be different than both of those predictions (e.g., if user 209A does not agree with either of the static or dynamic model predictions). As illustrated in FIG. 3A, user 209A has interacted with prediction drop-down box 341A to update user interface 301A with her own prediction (i.e., the assessment by user 209A that Patient A suffers from severe osteoarthritis).

Notes text box 342A enables user 209A to specify and/or record notes relating to her diagnosis. Prediction selection controls 343A enable user 209A to choose whether to use local data 252 and local prediction 253 (collectively "local training data 254") as new training data to update progressive model 232.

In the example shown in FIG. 3A, static model prediction 241 and progressive model prediction 242 are the same. In some examples, static model 231 and progressive model 232 may be the same or very similar models, and therefore, might be expected to make the same prediction. Note, however, the diagnosis made by user 209A happens to be different than the diagnosis made by both static model 231 and progressive model 232. Accordingly, user 209A apparently disagrees with the prediction made by static model 231 and progressive model 232. At least in that sense, user 209A may view static model 231 and progressive model 232 as not being particularly accurate or reliable, since her own judgment indicates that Patient A's knee suffers from severe osteoarthritis, yet static model 231 and progressive model 232 failed to reach the same conclusion.

Computing system 210A may update progressive model 232 based on local training data 254. For instance, referring again to FIG. 2 and FIG. 3A, input device 216 detects input that user interface module 224 determines corresponds to interactions with user interface 301A. User interface module 224 further determines that the interactions indicate that the "Yes" radio button included within prediction selection controls 343A has been selected (e.g., by cursor 302). In response to such interactions, user interface module 224 outputs information to model administration module 222. Model administration module 222 determines that progressive model 232 is to be updated using local training data 254 as a new training example. Note that local training data 254 includes local data 252, local prediction 253, and in some examples, may include data entered within notes text box 342A by or on behalf of user 209A. Model administration module 222 causes preprocessing module 221 to perform preprocessing tasks on local training data 254 to ensure that local training data 254 is in a form that can be used to properly train or retrain progressive model 232. After preprocessing performed by preprocessing module 221, model administration module 222 retrains progressive model 232 to take into account local training data 254. In some examples, retraining is done at computing system 210A using locally-available processing capabilities. In other examples, however, the retraining of progressive model 232 may be performed by another system or device (e.g., a system or device available over network 205), typically at the direction of model administration module 222.

Once retrained, progressive model 232 is available to make further predictions, and since progressive model 232 has been retrained using local training data 254, progressive model 232 may, in certain circumstances, make different predictions than the previous version of progressive model 232 when presented with input data corresponding to local data 252. In the example being described, static model 231 is not retrained, and thus would be expected to operate as before, and make the same predictions when presented with the same input data.

Computing system 210A may later receive new data for processing by static model 231 and progressive model 232. For instance, referring again to the example being described in connection with FIG. 2, user 209A may collect medical information for a new patient ("Patient B"), and present the medical information to computing system 210A as input. Input device 216 may detect input that user interface module 224 determines corresponds to a request to perform a new diagnosis on a patient (i.e., "Patient B"). User interface module 224 outputs information about the input to model administration module 222. Model administration module 222 determines that the input includes image information that can be used to enable static model 231 and progressive model 232 to make a diagnosis and/or prediction about whether severe osteoarthritis is present in Patient B's knee. Model administration module 222 outputs the image information to static model 231, and causes static model 231 to be applied to the image information to generate a new static model prediction 241. Model administration module 222 also outputs the image information to progressive model 232, and causes progressive model 232 to be applied to image information to generate a new progressive model prediction 242.

Computing system 210A may present information about the new predictions in a user interface. For instance, still referring to FIG. 2 and now also referring to FIG. 3B, model administration module 222 outputs to user interface module 224 information about the new static model prediction 241 generated by static model 231 and the new progressive model prediction 242 generated by progressive model 232. In response, user interface module 224 uses the information to generate data sufficient to render a new user interface on display device 300. User interface module 224 causes display device 300 to present user interface 301B as illustrated in FIG. 3B.

In FIG. 3B, user interface 301B includes profile region 310B, static model region 320B, dynamic model region 330B, and qualifier region 340B. As in FIG. 3A, profile region 310B identifies the patient being evaluated, describes a time and an operator and/or qualifier (e.g., user 209A or "Doctor A"), and provides information about what type of diagnosis is being performed. Static model region 320B and dynamic model region 330B provide information about the new predictions or diagnoses made by static model 231 (static model prediction 241) and progressive model 232 (progressive model prediction 242) for Patient B.

Note that in the example shown in FIG. 3B, static model 231 has predicted that severe osteoarthritis is not present in Patient B, yet progressive model 232 has predicted that severe osteoarthritis is present in Patent B. Static model prediction 241 and progressive model prediction 242 differ because static model 231 and progressive model 232 are now different models. Static model 231 and progressive model 232 may have initially been the same model, but as described above in connection with FIG. 3A, progressive model 232 has been retrained with at least one new training example (i.e., local training data 254), whereas static model 231 was not retrained with that training example. Accordingly, static model 231 and progressive model 232 might be expected to at least occasionally make differing predictions. In the example being described, the differences in the predictions made by static model 231 and progressive model 232 for Patient B might be a result of having retrained progressive model 232 with local training data 254.

In addition, progressive model 232 may occasionally, periodically, and/or continually be further updated with additional training examples. For instance, user 209A may perform a diagnosis for Patient B, and update prediction drop-down box 341B with the diagnosis, thereby identifying a preferred prediction for Patient B. User 209A may, in a manner similar to that illustrated in FIG. 3A, select "Yes" using prediction selection controls 343B to cause computing system 210A to further retrain progressive model 232. Such further retaining of progressive model 232 may be based on an additional training example derived from the data collected from Patient B and the preferred prediction specified by user 209A in drop-down box 341B. In such an example, preprocessing module 221 of user 209A preprocesses data associated with Patient B, and model administration module 222 retrains progressive model 232 with the new training example derived from the data associated with Patient B. Computing system 210A may further retrain and refine progressive model 232 over time, retraining progressive model 232 with new training examples as such training examples become available.

In some examples, such training examples may be derived from diagnoses that user 209A encounters, such as those she makes in her day to day medical practice. In some examples, user 209A may retrain progressive model 232 with each new relevant diagnosis she makes, by presenting input corresponding to each of her diagnoses. In other examples, user 209A may retrain progressive model 232 with a subset of the new diagnoses she makes.

Further, in still other examples, computing system 210A may be alternatively or additionally retrained using training examples derived from information received from other sources. For instance, in an example that can be described with reference to FIG. 2, one or more of the other computing systems 210 output signals over network 205. As shown in FIG. 2, computing system 210D, for example, may output remote training data 264 over network 205. Communication unit 215 of computing system 210A detects one or more signals over network 205. Communication unit 215 outputs information about the signals to model administration module 222. Model administration module 222 determines that the signals correspond to information sent over network 205 by one or more of the other computing systems 210. Model administration module 222 further determines that the signals include remote training data 264. Model administration module 222 outputs information about remote training data 264 to preprocessing module 221. Model administration module 222 receives one or more instances of training data 228 from preprocessing module 221 after processing by preprocessing module 221. Model administration module 222 may store such instances of training data 228 within data store 229.

Computing system 210A may present information about diagnoses, training examples, and/or information from other sources. For instance, continuing with the example being described with reference to FIG. 2 and now also referring to FIG. 3C, model administration module 222 outputs information about one or more instances of training data 228 to user interface module 224. User interface module 224 generates information sufficient to render a user interface describing the information. User interface module 224 causes display device 300 to present user interface 301C as illustrated in FIG. 3C.

In FIG. 3C, user interface 301C includes profile region 310C and qualifier table 350C. Profile region 310C identifies a person serving as a qualifier, which in the example shown in FIG. 3C, is "Doctor A" or user 209A. Qualifier table 350C provides information about additional training examples (e.g., including remote training data 264) that may be used to further refine or train progressive model 232. Qualifier table 350C provides information about the source of such data (doctor, hospital, clinic, or other source) along with the diagnosis made, and the date the diagnosis was made. Each row of 350C corresponds to one or more potential training examples that might be used to further refine progressive model 232. In some examples, qualifier table 350C may include one or more instances of local training data 254.

The right-most column of qualifier table 350C provides a checkbox for each such potential training example. By selecting a checkbox for a given row, user 209A (i.e., "Doctor A" or a person acting on her behalf) can select which of the training examples in qualifier table 350C should be used to retrain progressive model 232. In some examples, qualifier table 350C may include further information about each new training example. Such information may include additional information about the source (e.g., the name of the doctor making the diagnoses, further information about the background, credentials, or training of the doctor or doctors involved, or further information about the reputation, practice, location, or history of a specific hospital or clinic). Such information may include additional information about the diagnosis (e.g., any notes included by a doctor associated with the diagnosis). Such information may be included in qualifier table 350C, and/or may be accessible through qualifier table 350C (e.g., via further interaction with qualifier table 350C or through a link included within qualifier table 350C). In the example of FIG. 3C, therefore, user 209A may thus act as a qualifier that chooses which of the potential new training examples should be used to update progressive model 232.

Computing system 210A may be updated based on selections made by a qualifier. For instance, continuing with the example being described in connection with FIG. 2 and FIG. 3C, input device 216 detects input and outputs information about the input to user interface module 224. User interface module 224 determines that the input corresponds to selection of button 360C in user interface 301C. User interface module 224 outputs to qualifier module 223 information about the state of qualifier table 350C. Qualifier module 223 determines that the input indicates that four training examples identified by qualifier table 350C have been selected for use in retraining progressive model 232 (as shown in qualifier table 350C, checkboxes associated with two diagnoses from "Doctor B," one diagnosis from "Doctor C," and one diagnosis from the "Green Clinic" are selected).

Qualifier module 223 accesses training data 228 associated with each training example. In some examples, in order to access training data 228 associated with each training example, qualifier module 223 of computing system 210A may access one or more instances of training data 228 from data store 229. In other examples, qualifier module 223 may access one or more instances of training data 228 associated with the selected training examples by causing communication unit 215 to retrieve the relevant information over network 205. In such an example, qualifier module 223 may cause qualifier module 223 to retrieve the relevant information over network 205 from one or more of computing systems 210. Alternatively, or in addition, qualifier module 223 may cause qualifier module 223 to retrieve the relevant information over network 205 from clearinghouse 260, which may serve as a repository and/or centralized resource for such information.

Once qualifier module 223 accesses the appropriate instances of training data 228, qualifier module 223 causes model administration module 222 to retrain progressive model 232 using each selected training example in qualifier table 350C. Once retrained, progressive model 232 is available to make further predictions, and such predictions may differ from predictions made by a prior version of progressive model 232.

Progressive model 232 may continue to be retrained in a similar manner as new training examples become available through remote or other sources. For instance, still referring to the example being described with reference to FIG. 2 and FIG. 3C, computing system 210A may occasionally, periodically, or continually receive information from remote sources. User 209A may occasionally, periodically, or continually review such information, perhaps in a form similar to that illustrated in FIG. 3C. Computing system 210A may detect interactions with a user interface having the form illustrated in FIG. 3C, and determine that the interactions correspond to selections, by a qualifier, of available training data. Computing system 210A may, responsive to such selections, retrain progressive model 232 using the selected training data.

Although user 209A has been described as performing the task of qualifying potentially new training data available from other sources, in some examples, qualifier model 233 may be trained to perform such a task. For instance, in an example that can be described with reference to FIG. 2 and FIG. 3C, communication unit 215 occasionally detects input that qualifier module 223 determines corresponds to information (e.g., from clearinghouse 260 and/or from one or more of other computing systems 210) that can be used as a potential new set of additional training examples. Each time a new set of additional training examples is available, user interface module 224 presents information about the training examples in a user interface, which may have a form similar to user interface 301C of FIG. 3C. User interface module 224 detects interactions with such user interfaces. User interface module 224 outputs to qualifier module 223 information about such interactions. Qualifier module 223 determines that such interactions correspond to a user's selection of particular training examples from each corresponding set of training examples. Each time the user makes such selections, qualifier module 223 stores information about the selections in data store 229.

Eventually, qualifier module 223 may determine that there is sufficient information about selections made by user 209A to generate a machine learning model to mimic the predictions made by user 209A. For instance, still referring to FIG. 2, qualifier module 223 accesses information about selections made by user 209A. Qualifier module 223 uses the information to generate qualifier model 233. In some examples, qualifier module 223 may notice that user 209A always accepts new training examples from specific named doctors, clinics or hospitals, or from doctors, clinics, or hospitals having specific training, educational backgrounds, or other attributes. In such an example, qualifier module 223 may generate qualifier model 233 such that new training examples available from those specific doctors, clinics or hospitals tend to be selected by qualifier model 233. Similarly, qualifier module 223 may determine that user 209A never accepts new training examples from specific doctors, clinics or hospitals, or from doctors, clinics, or hospitals having specific attributes. In such an example, qualifier model 233 may generate qualifier model 233 such that new training examples available from those particular doctors, clinics or hospitals tend not to be selected by qualifier model 233. Once created, qualifier model 233 may perform the function of qualifying new training data available from other sources, and thus may relieve user 209A from performing such a task in at least some instances.

In some examples, computing system 210A may serve as a source of training examples for other computing systems 210 on network 205. For instance, again referring to FIG. 2, communication unit 215 of computing system 210A may output information derived from diagnoses made by an operator of computing system 210A (e.g., user 209A or "Doctor A") over network 205. Other computing systems 210 on network 205 may receive such information and process the information in a manner similar to how computing system 210A has been described as processing potential new training data (e.g., remote training data 264) available from remote sources. In some examples, an operator of computing system 210A may choose whether to enable such publication of diagnosis information to others by selection of the checkbox shown in profile region 310C of FIG. 3C. In some examples, computing system 210A may make all information about diagnoses made by user 209A or other operators of computing system 210 available to other computing systems 210 or to clearinghouse 260. In other examples, computing system 210A may make a subset of such diagnoses available to other computing systems 210 or to clearinghouse 260.

FIG. 3D illustrates a user interface that is similar to the user interface of FIG. 3A, except that FIG. 3D illustrates how predictions of a particular stage of osteoarthritis may be presented within a user interface. In other words, rather than predicting whether or not a patient has severe osteoarthritis, as illustrated FIG. 3A, FIG. 3D shows the predicted likelihood that a given patient has each stage of osteoarthritis. FIG. 3D thus illustrates that predictions need not be binary in nature (a particular condition is "present" or "not present"), but instead, can be associated with a range of values. Note in the example of FIG. 3D, prediction drop-down box 341D enables selection of a preferred prediction, which takes the form in this example of a particular stage osteoarthritis (e.g., normal, minor, mild, moderate, or severe).

Modules illustrated in FIG. 2 (e.g., preprocessing module 221, model administration module 222, qualifier module 223, user interface module 224, static model 231, progressive model 232, qualifier model 233) and/or illustrated or described elsewhere in this disclosure may perform operations described using software, hardware, firmware, or a mixture of hardware, software, and firmware residing in and/or executing at one or more computing devices. For example, a computing device may execute one or more of such modules with multiple processors or multiple devices. A computing device may execute one or more of such modules as a virtual machine executing on underlying hardware. One or more of such modules may execute as one or more services of an operating system or computing platform. One or more of such modules may execute as one or more executable programs at an application layer of a computing platform. In other examples, functionality provided by a module could be implemented by a dedicated hardware device.

Although certain modules, data stores, components, programs, executables, data items, functional units, and/or other items included within one or more storage devices may be illustrated separately, one or more of such items could be combined and operate as a single module, component, program, executable, data item, or functional unit. For example, one or more modules or data stores may be combined or partially combined so that they operate or provide functionality as a single module. Further, one or more modules may interact with and/or operate in conjunction with one another so that, for example, one module acts as a service or an extension of another module. Also, each module, data store, component, program, executable, data item, functional unit, or other item illustrated within a storage device may include multiple components, sub-components, modules, sub-modules, data stores, and/or other components or modules or data stores not illustrated.

Further, each module, data store, component, program, executable, data item, functional unit, or other item illustrated within a storage device may be implemented in various ways. For example, each module, data store, component, program, executable, data item, functional unit, or other item illustrated within a storage device may be implemented as a downloadable or pre-installed application or "app." In other examples, each module, data store, component, program, executable, data item, functional unit, or other item illustrated within a storage device may be implemented as part of an operating system executed on a computing device.

Figure 4:
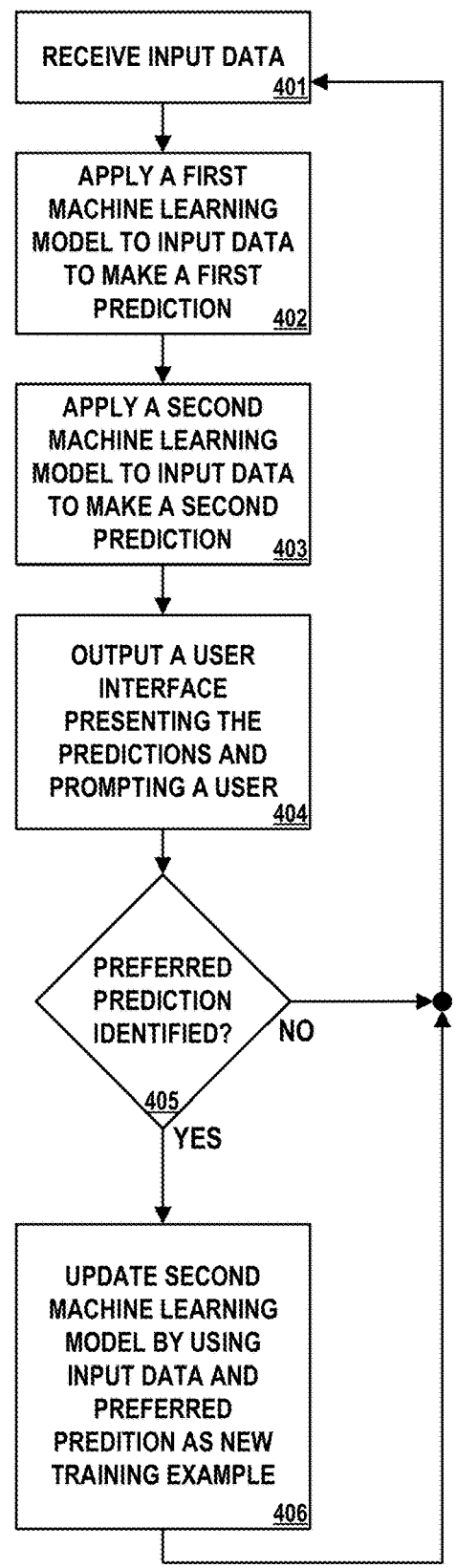
FIG. 4 is a flow diagram illustrating operations performed by an example computing system in accordance with one or more aspects of the present disclosure.

FIG. 4 is a flow diagram illustrating operations performed by an example computing system in accordance with one or more aspects of the present disclosure. FIG. 4 is described below within the context of computing system computing system 210A of FIG. 2. In other examples, operations described in FIG. 4 may be performed by one or more other components, modules, systems, or devices. Further, in other examples, operations described in connection with FIG. 4 may be merged, performed in a difference sequence, omitted, or may encompass additional operations not specifically illustrated or described.

In the process illustrated in FIG. 4, and in accordance with one or more aspects of the present disclosure, computing system 210 may detect input data (401). For example, with reference to FIG. 2, input device 216 of computing system 210A may detect input that user interface module 224 determines corresponds to information derived from interactions with a user interface presented by computing system 210A. User interface module 224 outputs information about the interactions to model administration module 222. Model administration module 222 determines that the interactions include input data that can be used by a model to make a prediction.

Computing system 210A may apply a first machine learning model to input data (402). Model administration module 222 presents the input data to static model 231. Static model 231 generates static model prediction 241 based on the input data.

Computing system 210A may apply a second machine learning model to the input data (403). For example, again referring to FIG. 2, model administration module 222 also presents the input data derived from the interactions with the user interface to progressive model 232. Progressive model 232 generates progressive model prediction 242 based on the input data.

Computing system 210A may output a user interface presenting information about the first prediction and the second prediction, and prompting a user to identify a preferred prediction (404). For example, model administration module 222 outputs information about static model prediction 241 and progressive model prediction 242 to user interface module 224. User interface module 224 causes output device 217 to present a user interface, such as that illustrated in FIG. 3D. In FIG. 3D, display device 300 (i.e., one of output devices 217) presents static model prediction 241 in static model region 320D, presents progressive model prediction 242 in dynamic model region 330D, and prompts a user to identify a preferred prediction in qualifier region 340D.

Computing system 210A may determine that the user has not selected a preferred prediction (NO path from 405). In such an example, computing system 210A might not update the second machine learning module in this instance.

In other examples, however, computing system 210A may determine that the user has selected a preferred prediction (YES path from 405). For instance, in the latter example, input device 216 detects input that user interface module 224 determines corresponds to an interaction with prediction drop-down box 341D of FIG. 3D. User interface module 224 outputs information about the interaction to model administration module 222. Model administration module 222 determines that the user has selected a preferred prediction.

Computing system 210A may, responsive to receiving input identifying a preferred prediction, update the second machine learning model by using the input data and the preferred prediction as a new training example (406). For example, input device 216 detects input that user interface module 224 determines corresponds to information about a user's preferred prediction. User interface module 224 outputs information about the preferred prediction to model administration module 222. Model administration module 222 causes preprocessing module 221 to preprocess the originally-received input data and the preferred prediction. Model administration module 222 retrains progressive model 232 using the preprocessed input data and the preferred prediction as a new training example.

For processes, apparatuses, and other examples or illustrations described herein, including in any flowcharts or flow diagrams, certain operations, acts, steps, or events included in any of the techniques described herein can be performed in a different sequence, may be added, merged, or left out altogether (e.g., not all described acts or events are necessary for the practice of the techniques). Moreover, in certain examples, operations, acts, steps, or events may be performed concurrently, e.g., through multi-threaded processing, interrupt processing, or multiple processors, rather than sequentially. Further certain operations, acts, steps, or events may be performed automatically even if not specifically identified as being performed automatically. Also, certain operations, acts, steps, or events described as being performed automatically may be alternatively not performed automatically, but rather, such operations, acts, steps, or events may be, in some examples, performed in response to input or another event.

For ease of illustration, a limited number of systems, devices, or organizations (e.g., computing systems 210, clearinghouses 260, developers 270, as well as others) are shown within the Figures and/or in other illustrations referenced herein. However, techniques in accordance with one or more aspects of the present disclosure may be performed with many more of such systems, components, devices, modules, and/or other items, and collective references to such systems, components, devices, modules, and/or other items may represent any number of such systems, components, devices, modules, and/or other items.

The Figures included herein each illustrate at least one example implementation of an aspect of this disclosure. The scope of this disclosure is not, however, limited to such implementations. Accordingly, other example or alternative implementations of systems, methods or techniques described herein, beyond those illustrated in the Figures, may be appropriate in other instances. Such implementations may include a subset of the devices and/or components included in the Figures and/or may include additional devices and/or components not shown in the Figures.

The detailed description set forth above is intended as a description of various configurations and is not intended to represent the only configurations in which the concepts described herein may be practiced. The detailed description includes specific details for the purpose of providing a sufficient understanding of the various concepts. However, these concepts may be practiced without these specific details. In some instances, well-known structures and components are shown in block diagram form in the referenced figures in order to avoid obscuring such concepts.

Accordingly, although one or more implementations of various systems, devices, and/or components may be described with reference to specific Figures, such systems, devices, and/or components may be implemented in a number of different ways. For instance, one or more devices illustrated in the Figures herein as separate devices may alternatively be implemented as a single device; one or more components illustrated as separate components may alternatively be implemented as a single component. Also, in some examples, one or more devices illustrated in the Figures herein as a single device may alternatively be implemented as multiple devices; one or more components illustrated as a single component may alternatively be implemented as multiple components. Each of such multiple devices and/or components may be directly coupled via wired or wireless communication and/or remotely coupled via one or more networks. Also, one or more devices or components that may be illustrated in various Figures herein may alternatively be implemented as part of another device or component not shown in such Figures. In this and other ways, some of the functions described herein may be performed via distributed processing by two or more devices or components.

Further, certain operations, techniques, features, and/or functions may be described herein as being performed by specific components, devices, and/or modules. In other examples, such operations, techniques, features, and/or functions may be performed by different components, devices, or modules. Accordingly, some operations, techniques, features, and/or functions that may be described herein as being attributed to one or more components, devices, or modules may, in other examples, be attributed to other components, devices, and/or modules, even if not specifically described herein in such a manner.

Although specific advantages have been identified in connection with descriptions of some examples, various other examples may include some, none, or all of the enumerated advantages. Other advantages, technical or otherwise, may become apparent to one of ordinary skill in the art from the present disclosure. Further, although specific examples have been disclosed herein, aspects of this disclosure may be implemented using any number of techniques, whether currently known or not, and accordingly, the present disclosure is not limited to the examples specifically described and/or illustrated in this disclosure.

What is claimed is:

1. A method comprising:
    applying, by a computing system, a first machine learning model to input data to make a first prediction in a subject matter field;
    applying, by the computing system, a second machine learning model to the input data to make a second prediction in the subject matter field, wherein the second machine learning model is derived from the first machine learning model by starting with the first machine learning model and training the second machine learning model with additional training examples;
    outputting, by the computing system, a first user interface that presents information about the first prediction and the second prediction and prompts a user that is an expert in the subject matter field to make a local prediction while reviewing the first prediction and the second prediction, and wherein the local prediction is an independent prediction based on the user's expertise in the subject matter field;
    responsive to receiving input identifying the local prediction, generating, by the computing system, an additional training example based on the local prediction;
    retraining, by the computing system, the second machine learning model using the additional training example;
    receiving, by the computing system and over a network from one or more peer systems, information about a plurality of peer training examples, wherein each of the peer training examples is based on a prediction in the subject matter field made by another expert;
    outputting, by the computing system, a second user interface that prompts the user to qualify each of the peer training examples for use in retraining, wherein the second user interface presents, for each peer training example, information about the peer training example, including an identity of an expert associated with the peer training example and a prediction associated with the peer training example; and
    responsive to receiving input qualifying one of the peer training examples, further retraining, by the computing system, the second machine learning model using the qualified peer training example.

2. The method of claim 1, further comprising:
    receiving, by the computing system and over a network, information about further additional training examples; and
    updating, by the computing system, the second machine learning model by further retraining the second machine learning model using a subset of the further additional training examples.

3. The method of claim 2, further comprising:
    presenting, by the computing system, a third user interface including the further additional training examples; and
    detecting, by the computing system, a series of indications of input selecting the subset of the further additional training examples.

4. The method of claim 1, further comprising:
    training, by the computing system, a third machine learning model to select, from a set of further additional training examples, a subset of the further additional training examples.

5. The method of claim 4, wherein training the third machine learning model includes:
    detecting a series of indications of input representing user selections qualifying training examples from among a set of historical training examples; and
    training the third machine learning model based on the series of indications of input.

6. The method of claim 4, further comprising:
    updating, by the computing system, the second machine learning model by further retraining the second machine learning model using the subset of the further additional training examples.

7. The method of claim 1, further comprising:
    receiving, by the computing system and over the network, information about a new set of additional training examples;
    selecting, by a third machine learning model trained to qualify training examples, a subset of the new set of additional training examples; and
    updating, by the computing system, the second machine learning model by further retraining the second machine learning model using the subset of the new set of additional training examples.

8. The method of claim 1, wherein outputting the first user interface includes prompting the user to make the local prediction by choosing from among the first prediction and the second prediction.

9. The method of claim 1, wherein the first prediction is the same as the second prediction, wherein the input data is a first set of input data, the method further comprising:
 applying by the computing system, the first machine learning model to a second set of input data to make a third prediction;
 applying, by the computing system, the retrained second machine learning model to the second set of input data to make a fourth prediction; and
 outputting, by the computing system, a third user interface presenting information about the third prediction and the fourth prediction, wherein the third prediction is different from the fourth prediction.

10. The method of claim 2, wherein receiving information about further additional training examples includes:
 receiving, from one of the peer systems, information identifying attributes about the further additional training examples.

11. The method of claim 10, wherein the attributes about the further additional training examples identify:
 an organization that created data on which the further additional training examples are based.

12. The method of claim 2, wherein receiving information about further additional training examples includes:
 receiving further additional training examples from within an organization that operates the computing system.

13. The method of claim 1, wherein the first machine learning model and the second machine learning model are trained to make medical diagnoses based on medical data.

14. The method of claim 1, wherein the first machine learning and the second machine learning model are trained to make an investment decision based on financial data,
 wherein the investment decision includes one of recommending an investment selection, making a stock selection, making an investment allocation selection.

15. A system comprising:
 a storage system; and
 processing circuitry having access to the storage system and configured to:
 apply a first machine learning model to input data to make a first prediction in a subject matter field,
 apply a second machine learning model to the input data to make a second prediction in the subject matter field, wherein the second machine learning model is derived from the first machine learning model by starting with the first machine learning model and training the second machine learning model with additional training examples,
 output a first user interface that presents information about the first prediction and the second prediction and prompts a user that is an expert in the subject matter field to make a local prediction while reviewing the first prediction and the second prediction, and wherein the local prediction is an independent prediction based on the user's expertise in the subject matter field,
 responsive to receiving input identifying the local prediction, generate an additional training example based on the local prediction,
 update the second machine learning model by using the additional training example,
 receive, over a network from one or more peer systems, information about a plurality of peer training examples, wherein each of the peer training examples is based on a prediction in the subject matter field made by another expert,
 output a second user interface that prompts the user to qualify each of the peer training examples for use in retraining, wherein the second user interface presents, for each peer training example, information about the peer training example, including an identity of an expert associated with the peer training example and a prediction associated with the peer training example, and
 responsive to receiving input qualifying one of the peer training examples, further retrain the second machine learning model using the qualified peer training example.

16. The system of claim 15, wherein the processing circuitry is further configured to:
 receive, over a network from a clearinghouse, information about further additional training examples; and
 update the second machine learning model by further retraining the second machine learning model using a subset of the further additional training examples.

17. The system of claim 16, wherein the processing circuitry is further configured to:
 present a third user interface including the further additional training examples; and
 detect a series of indications of input selecting the subset of the further additional training examples.

18. A non-transitory computer-readable storage medium comprising instructions that, when executed, configure processing circuitry of a computing system to:
 apply a first machine learning model to input data to make a first prediction in a subject matter field;
 apply a second machine learning model to the input data to make a second prediction in the subject matter field, wherein the second machine learning model is derived from the first machine learning model by starting with the first machine learning model and training the second machine learning model with additional training examples;
 output a first user interface presenting information about the first prediction and the second prediction and prompting a user that is an expert in the subject matter field to make a local prediction while reviewing the first prediction and the second prediction, and wherein the local prediction is an independent prediction based on the user's expertise in the subject matter field;
 responsive to receiving input identifying the local prediction, generate an additional training example based on the prediction;
 update the second machine learning model by using the additional training example,
 receive, over a network from one or more peer systems, information about a plurality of peer training examples, wherein each of the peer training examples is based on a prediction in the subject matter field made by another expert;
 output a second user interface that prompts the user to qualify each of the peer training examples for use in retraining, wherein the second user interface presents, for each peer training example, information about the peer training example, including an identity of an expert associated with the peer training example and a prediction associated with the peer training example; and responsive to receiving input qualifying one of the peer training examples, further retrain the second machine learning model using the qualified peer training example.

* * * * *